United States Patent

Porcheron et al.

(10) Patent No.: US 9,486,738 B2
(45) Date of Patent: Nov. 8, 2016

(54) CAPTURE MASS COMPOSED OF ELEMENTAL SULPHUR DEPOSITED ON A POROUS SUPPORT FOR CAPTURING HEAVY METALS

(71) Applicant: IFP Energies Nouvelles, Rueil-Malmaison (FR)

(72) Inventors: Fabien Porcheron, Mions (FR); Karin Barthelet, Lyons (FR); Arnaud Baudot, Vernaison (FR); Marc-Antoine Lelias, Ales (FR); Alexandre Nicolaos, Courbevoie (FR); Tiziana Armaroli, Paris (FR); Clotilde Jubin, Boulogne Billancourt (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 490 days.

(21) Appl. No.: 13/924,740

(22) Filed: Jun. 24, 2013

(65) Prior Publication Data

US 2013/0341564 A1    Dec. 26, 2013

(30) Foreign Application Priority Data

Jun. 26, 2012 (FR) ...................... 12 01811

(51) Int. Cl.
*B01D 53/64* (2006.01)
*B01J 35/10* (2006.01)
(Continued)

(52) U.S. Cl.
CPC ............ *B01D 53/64* (2013.01); *B01J 20/0266* (2013.01); *B01J 20/08* (2013.01); *B01J 20/2808* (2013.01); *B01J 20/28071* (2013.01); *B01J 20/28083* (2013.01); *B01J 20/3234* (2013.01); *B01J 27/04* (2013.01); *B01J 35/108* (2013.01); *B01J 35/1038* (2013.01); *B01J 35/1066* (2013.01); *B01J 37/0207* (2013.01); *C07C 7/12* (2013.01);
(Continued)

(58) Field of Classification Search
CPC ..... B01D 53/64; B01J 20/08; B01J 20/3234; C07C 7/12
See application file for complete search history.

(56) References Cited

U.S. PATENT DOCUMENTS 5,244,648 A * 9/1993 Dupin .................. B01D 53/945
  23/313 R
6,033,556 A * 3/2000 Didillon .................... B01J 20/02
  208/253

FOREIGN PATENT DOCUMENTS

EP    0055164 A1    6/1982
EP    0107582    * 10/1983
(Continued)

OTHER PUBLICATIONS

Machine Translation of EP0107582.*
(Continued)

*Primary Examiner* — Peter F Godenschwager
*Assistant Examiner* — Andrew J Oyer
(74) *Attorney, Agent, or Firm* — Millen White Zelano and Branigan, PC; Csaba Henter; Anthony Zelano

(57) ABSTRACT

The present invention concerns the elimination of heavy metals, in particular mercury and possibly arsenic and lead, present in a dry or moist gaseous effluent (1) by means of a capture mass (2) comprising a porous support at least part of which is of low mesoporosity and an active phase based on sulphur. The invention is advantageously applicable to the treatment of gas of industrial origin, synthesis gas or natural gas.

20 Claims, 2 Drawing Sheets

(51) Int. Cl.
  *B01J 37/02* (2006.01)
  *B01J 27/04* (2006.01)
  *B01J 20/32* (2006.01)
  *C07C 7/12* (2006.01)
  *B01J 20/08* (2006.01)
  *B01J 20/28* (2006.01)
  *B01D 53/26* (2006.01)
  *B01D 53/82* (2006.01)
  *B01J 20/02* (2006.01)

(52) U.S. Cl.
  CPC .......... *B01D 53/261* (2013.01); *B01D 53/263* (2013.01); *B01D 53/82* (2013.01); *B01D 2251/304* (2013.01); *B01D 2251/608* (2013.01); *B01D 2252/2023* (2013.01); *B01D 2253/104* (2013.01); *B01D 2253/106* (2013.01); *B01D 2253/108* (2013.01); *B01D 2253/1124* (2013.01); *B01D 2253/306* (2013.01); *B01D 2253/31* (2013.01); *B01D 2253/311* (2013.01); *B01D 2255/20707* (2013.01); *B01D 2255/20715* (2013.01); *B01D 2256/24* (2013.01); *B01D 2256/245* (2013.01); *B01D 2257/60* (2013.01); *B01D 2257/602* (2013.01); *B01D 2257/80* (2013.01); *B01D 2258/0283* (2013.01); *B01J 2220/56* (2013.01)

(56) References Cited

FOREIGN PATENT DOCUMENTS

| EP | 0107582 | A1 | | 5/1984 |
|---|---|---|---|---|
| FR | 2529802 | | * | 7/1982 |
| FR | 2529802 | A1 | | 1/1984 |

OTHER PUBLICATIONS

Machine Translation of FR2529802.*
Search Report and Written Opinion from Priority Application No. FR1201881 dated Mar. 27, 2013.
Patrick Euzen et al. "Alumina" In: "Handbook of Porous Solids" [Apr. 25, 2008] Wiley-VCH Verlag GmbH, pp. 1591-1677.
English Abstract for FR2529802A1 dated Jan. 13, 1984.
English Abstract for EP0107582A1 dated May 2, 1984.
English Abstract for EP0055164A1 dated Jun. 30, 1982.

* cited by examiner

CAPTURE MASS COMPOSED OF ELEMENTAL SULPHUR DEPOSITED ON A POROUS SUPPORT FOR CAPTURING HEAVY METALS

The present invention relates to the elimination of heavy metals, in particular mercury and possibly arsenic and lead, present in a dry or moist gaseous effluent by means of a capture mass comprising a porous support at least part of which is of low mesoporosity and an active phase based on elemental sulphur. The invention is advantageously applicable to the treatment of gas of industrial origin, synthesis gas or natural gas.

Mercury is a metallic contaminant which is found in gaseous or liquid hydrocarbons produced in many regions of the world, such as the Gulf of Niger, South America, North Africa or the Asia-Pacific region.

Eliminating mercury from hydrocarbon cuts is industrially desirable for several reasons:
 the safety of the operators, since elemental mercury is volatile and presents serious risks of neurotoxicity by inhalation, while organic forms of mercury present similar risks by skin contact;
 and also for reasons of preventing the deactivation of heterogeneous catalysts used to upgrade such liquid hydrocarbon cuts. Mercury causes sintering, by amalgamation, of the nanoparticles of noble metals—such as platinum or palladium—deposited on a porous support which are used in various catalytic reactions such as the selective hydrogenation of olefins produced by steam cracking or catalytic cracking of liquid hydrocarbons. The massive reduction of the specific surface area of the component metallic particles of the catalysts results in a very substantial loss in their catalytic activity.

Industrially, the elimination of mercury from liquid or gaseous hydrocarbon cuts is carried out by circulating the effluent to be treated through guard beds filled with capture masses. This reaction is specific in that the impurity to be treated is then retained within or at the surface of the capture mass and the effluent evacuated from the bed of the capture mass is thus purified.

The capture of heavy metals such as mercury may be carried out easily by reacting the mercury with active sulphur-based phases. The document U.S. Pat. No. 7,645,306 B2 shows that elemental mercury)($Hg^{\circ}$) reduces copper sulphide, CuS, in an irreversible manner in accordance with the following:

$$Hg^{\circ}+2CuS \rightarrow Cu_2S+HgS.$$

The product formed, HgS, known as cinnabar or metacinnabar, has the specific feature of being chemically inert and solid over a vast temperature range. The mercury is thus trapped in the bed of the capture mass and the effluent to be treated is purified. These capture masses based on metallic sulphides are generally prepared by initially depositing an oxide precursor such as CuO, for example, then by applying a sulphurization step in order to transform the metallic oxide into a metallic sulphide.

In order to eliminate this sulphurization step, the direct use of an active phase, constituted by elemental sulphur, is possible. In fact, elemental sulphur, S, reacts with elemental mercury, $Hg^{\circ}$, in an irreversible manner as follows:

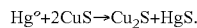
(1)

Reaction (1) is spontaneous and has a negative free energy ΔG (kJ/mole) over a wide temperature range, typically 0° C. to 150° C.

Conventionally, capture masses based on elemental sulphur are obtained by a method for impregnating elemental sulphur onto an activated carbon type support. As an example, the document U.S. Pat. No. 4,708,853 describes a method for the synthesis of capture masses during which solid elemental sulphur is brought into contact and mixed with activated carbon granules, then heated to a temperature of more than about T=150° C. for 10 to 90 minutes in order to liquefy the sulphur. The liquid sulphur then migrates into the porous veins of the activated carbon and then the solid is quenched in order to solidify the sulphur.

Activated carbon has the particular feature of being inexpensive, and so the cost of manufacturing capture masses is low. However, such porous supports suffer from a number of disadvantages in operational terms.

Firstly, activated carbon usually originates from residues obtained from the food industry (for example: coconut shells) or from the energy sector (for example: coal, coke) and thus has a porosity which can vary widely and is difficult to control. Thus, almost systematically, it will comprise a porosity which is termed microporous, i.e. with a pore size (i.e. the diameter d) not exceeding 2 nm (definition as given in the IUPAC nomenclature). The presence of such pores affects the performances of the guard bed of capture mass in the sense that diffusion of mercury in these pores is not favoured. Thus, the mercury takes more time to access the active sites and with a fixed contact time, the capture efficiency is found to be reduced.

In addition, the effluents to be treated often comprise a non-zero water content. The presence of water in the gas to be treated causes a phenomenon of condensation on the porous supports used which is known as capillary condensation. This phenomenon results in the appearance, at a given temperature, of liquid water at pressures below the saturated vapour pressure of water (P0). For a model pore with a cylindrical shape, Kelvin's equation (equation 2) can be used to determine the critical pore radius (Rc) beyond which the pores will be filled with liquid water.

$$Rc=-2\gamma V_m \cos \theta/RT/\log 10(P/P0) \quad (2)$$

where P is the pressure of the gas, T is the temperature of the gas, R is the ideal gas constant (R=8.314 J/K/mole), $V_m$ is the molar volume of the water, γ is the air/water surface tension and 8 is the water/solid contact angle. P/P0 corresponds to the definition of the relative humidity of the effluent. Smaller pores, in particular micropores (d<2 nm), are thus much more sensitive than mesopores (2<d<50 nm) or macropores (d>50 nm) to the capillary condensation phenomenon.

The capillary condensation mechanism may also occur with hydrocarbon vapours or volatile organic compounds.

The presence of capillary condensation has a major impact on the function of the capture mass, since it causes the appearance of a high resistance to the transfer of material in the bed and prevents the mercury from gaining access to the whole of the active phase. Very frequently, then, the performance of the guard bed is substantially altered. A drop in the performance of capture masses of the sulphur type on activated carbon has been observed during overnight functional operation of the guard bed. This dysfunction is attributed to the reduction in the temperature of the reactor at night-time, which involves the appearance of capillary condensation in the bed. Similarly, it has been shown that for a model gas (mercury in nitrogen) with a relative humidity of 10%, the performances of the capture mass based on sulphur deposited on activated carbon reduces by 25% (Mc Namara, J. D. & Wagner, N. J., Process effects on activated carbon performances and analytical methods used for low level mercury removal in natural gas applications, Gas Sep. Purif. 10 (2) 1996, 137-140).

This problem of hygrometric resistance thus means that either the effluent has to be reheated or the water has to be condensed by chilling upstream of the guard bed, which gives rise to high operational overcosts or by placing the mercury guard bed downstream of industrial driers used to remove water from the gas stream. However, those drying units often use compounds of the glycol type in which the mercury can dissolve. The document WO 2005/047438 in particular shows that the concentration of mercury in the glycol may reach high values, of the order of 2.9 ppm. During the regeneration step, the glycol solution is heated to temperatures close to T=200° C. and a portion of the mercury is then discharged into the atmosphere.

In addition, capture masses based on sulphur deposited on activated carbon are very often subject to problems with the stability under humid conditions, since the active phase may be entrained by the presence of water or liquid hydrocarbons. This peculiarity, linked to the weak energetic interaction existing between the active phase and the surface of the activated carbon and to the solubility of sulphur in such media, leads to a drastic fall in the service life of the capture masses.

The document EP 0 107 582 describes a capture mass based on sulphur on a porous support formed from alumina. The porous support comprises a high pore volume in the range 10 to 100 nm. However, the capture masses described in document EP 0 107 582 are sensitive to the phenomenon of entrainment of the active phase by the fluid to be treated; this phenomenon is also known as leaching.

The present invention proposes a capture mass composed of elemental sulphur deposited on an alumina support which is resistant to the phenomena of capillary condensation and of active phase entrainment.

In general, the present invention describes a capture mass for capturing mercury, said mass comprising an active phase deposited on a porous support, the active phase comprising elemental sulphur, the porous support having a pore volume $V_{0.004}>0.1$ mL/g, $V_{0.004}$ corresponding to the cumulative volumes of pores with a size of less than 0.004 µm, i.e. less than 4 nm.

In accordance with the invention, the porous support may be composed of at least one of the following oxides: alumina, titanium oxide, zirconium oxide and silicon oxide. Preferably, the porous support is composed of alumina.

The porous support may have a total pore volume in the range 0.3 to 1 cm$^3$/g, the porous support may have a BET specific surface area in the range 100 to 400 m$^2$/g, and the porous support may comprise a quantity of sodium in the range 10 to 5000 ppm by weight of $Na_2O$.

The porous support may have a pore volume $V_{0.002}<0.002$ mL/g, $V_{0.002}$ corresponding to the cumulative volumes of pores with a size of less than 0.002 µm, i.e. 2 nm.

The porous support may have a pore volume $V_{0.1}>0.2$ mL/g, $V_{0.1}$ corresponding to the cumulative volumes of pores with a size of less than 0.1 µm, i.e. 100 nm.

The porous support may have a pore volume $V_{0.1-0.01}<0.15$ mL/g, $V_{0.1-0.01}$ corresponding to the cumulative volumes of pores with a size in the range 0.1 µm to 0.01 µm, i.e. in the range 100 to 10 nm.

The active phase may comprise elemental sulphur $S_x$, x being in the range 1 to 30.

The quantity by weight of elemental sulphur with respect to the weight of the capture mass may be in the range 1% to 60%, and the quantity by weight of the porous support with respect to the weight of the capture mass may be in the range 40% to 99%.

The capture mass of the invention may be produced by depositing sulphur on the porous support. As an example, the sulphur may be deposited by bringing a sulphur powder into contact with the support or by bringing a sulphur vapour into contact with the support or by bringing sulphur in liquid solution into contact with the support, then by carrying out a drying step by heating the support containing the sulphur.

The present invention also concerns a process for eliminating mercury contained in a gaseous effluent, in which gaseous effluent is brought into contact with the capture mass in accordance with the invention.

Before contact, a drying operation may be carried out in order to reduce the relative humidity of the gaseous effluent. The drying operation may be carried out by means of contact with a water-adsorbing sieve, by means of contact with an absorbent solution comprising glycol, or by heating the gaseous effluent.

Contacting may be carried out at a temperature in the range −50° C. to 115° C. and at a pressure in the range 0.1 bar absolute to 200 bars absolute, and with an Hourly Space Velocity in the range 50 to 50000 h$^{-1}$.

In a variation of the process of the invention, the relative humidity of the gaseous effluent may be in the range 60% to 100%.

The gaseous effluent may be selected from: combustion fumes, a synthesis gas, a natural gas and a hydrocarbon effluent.

Surprisingly, the inventors have discovered that the use of capture masses in accordance with the invention based on elemental sulphur dispersed over a porous support at least part of which is of low mesoporosity can result in improved heavy metal adsorption performances, in particular for mercury. The function of the capture mass of the invention is not in fact altered by the presence of water vapour in the gas, even at high hygrometric levels. The use of the capture mass of the invention is of great importance in all processes for the treatment of dry or moist gaseous effluents in eliminating heavy metals, in particular mercury, present in these feeds; examples which may also be cited are arsenic and lead.

Further characteristics and advantages of the invention will become apparent from the following description made with reference to the accompanying drawings in which:

Figure 1:
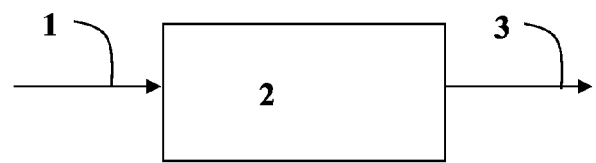
FIG. 1 is a diagrammatic representation of a process for capturing mercury, in accordance with the invention.

In the present description, under the IUPAC convention, the term "micropores" means pores with a diameter of less than 2 nm, i.e. 0.002 µm; the term "mesopores" means pores with a diameter of more than 2 nm, i.e. 0.002 µm and less than 50 nm, i.e. 0.05 µm, and the term "macropores" means pores with a diameter of more than 50 nm, i.e. 0.05 µm.

The present invention concerns a formulation for a capture mass for capturing heavy metals, in particular mercury, contained in a gaseous feed. The capture mass is composed of a porous support and an active phase composed of elemental sulphur. The active phase is deposited on the porous support.

Preferably, the proportion by weight of sulphur with respect to the weight of the capture mass is in the range 1% to 60%, preferably in the range 2% to 40% and highly preferably in the range 2% to 15%, or even in the range 2% to 10% or in the range 4% to 10%.

Preferably, the proportion by weight of porous support with respect to the weight of the capture mass is in the range 40% to 99%, preferably in the range 60% to 98% and highly preferably in the range 90% to 98%.

The active phase is composed of elemental sulphur, i.e. of molecules of sulphur which are not chemically bonded to another compound. The active phase may be elemental sulphur $S_x$, x being in the range 1 to 30, preferably in the range 4 to 20 and highly preferably equal to 8, 7, 6, 12 or 18, which corresponds to the most stable allotropic forms of elemental sulphur. The elemental sulphur composing the capture mass is selected for its property of being reactive with the heavy metals, in particular with mercury.

The composition of the porous support may be selected from alumina, silicon oxide, zirconium oxide, titanium oxide or any type of mixture of the oxides cited above. In accordance with the invention, the support is preferably composed of a porous alumina. Preferably, the support is substantially composed of alumina alone, i.e. the support comprises at least 95%, or even 98% or even 99% by weight of alumina with respect to the weight of the support.

The characteristics of the porous support of the capture mass of the invention mentioned in the present description correspond to the characteristics of the support before sulphur has been deposited on the support.

In the case in which the porous support is alumina, the alumina support may be synthesized by various methods which are known to the skilled person, for example by the methods described below.

First support synthesis method: rapid dehydration of a precursor of the aluminium trihydroxide ($Al(OH)_3$) type (also known as hydrargillite or gibbsite), for example obtained from the process generally known as the Bayer process, is carried out. Next, shaping is carried out, for example by granulation, then an optional hydrothermal treatment, then calcining, which results in the production of alumina. This method has been detailed in particular in the document by P. Euzen, P. Raybaud, X. Krokidis, H. Toulhoat, J. L. Le Loarer, J. P. Jolivet, C. Froidefond, Alumina, in Handbook of Porous Solids, Eds F. Schüth, K. S. W. Sing, J. Weitkamp, Wiley-VCH, Weinheim, Germany, 2002, pp. 1591-1677. This method can be used to produce an alumina which is usually known as flash alumina.

Second support synthesis method: a process for the production of a gel constituted by a precursor of the aluminium gamma-oxy(hydroxide) type (AlO(OH))—also known as boehmite) with high specific surface areas in the range 150 to 600 m²/g is carried out. Next, the gel is formed, for example by mixing-extrusion. Next, a series of heat treatments or optional hydrothermal treatments is carried out on the product, leading to the production of the alumina. The boehmite gel may, for example, be obtained by precipitation of basic and/or acidic solutions of aluminium salts induced by changing the pH or any other method which is known to the skilled person. This method has in particular been described in the document by P. Euzen, P. Raybaud, X. Krokidis, H. Toulhoat, J. L. Le Loarer, J. P. Jolivet, C. Froidefond, Alumina, in Handbook of Porous Solids, Eds F. Schüth, K. S. W. Sing, J. Weitkamp, Wiley-VCH, Weinheim, Germany, 2002, pp. 1591-1677.

Preferably, the first method is carried out in order to obtain the porous alumina support for the capture mass of the invention. Highly preferably, the first method described is carried out without carrying out any hydrothermal treatments so as to maximize the number of pores with a diameter in the range 0.002 to 0.004 μm. The preparation of the capture mass of the invention then comprises the following steps:

a) rapid dehydration of a precursor of the aluminium trihydroxide ($Al(OH)_3$) type (also known as hydrargillite or gibbsite), for example obtained from the process usually known as the Bayer process;
b) shaping the alumina, for example by granulation;
c) calcining the support between 250° C. and 600° C.

In accordance with the invention, the porous support has a pore volume $V_{0.004} > 0.1$ mL/g, $V_{0.004}$ corresponding to the cumulative volumes of pores with a size of less than 0.004 μm. The pore size corresponds to the diameter of an ideal theoretical pore which is assumed to be cylindrical. Preferably, a porous support is selected which has a pore volume $V_{0.004} > 0.12$ mL/g.

In addition, the pore support preferably has a pore volume $V_{0.01} > 0.2$ mL/g, $V_{0.01}$ corresponding to the cumulative volumes of pores with a size of less than 0.01 μm. The pore size corresponds to the diameter of an ideal theoretical pore which is assumed to be cylindrical. Preferably, a porous support is selected which has a pore volume $V_{0.01} > 0.025$ mL/g; more preferably, $V_{0.01} > 0.28$ mL/g.

The fact of having a high pore volume $V_{0.004}$, for example $V_{0.004} > 0.06$ mL/g, and optionally a pore volume $V_{0.01} > 0.2$ mL/g, i.e. the presence of small mesopores, means that sufficient sulphur can be confined in the pores for it not to be entrained with the effluent when using the capture mass, i.e. the phenomenon of leaching sulphur is completely avoided.

In accordance with the invention, the porous support preferably has a low pore volume composed of large mesopores and macropores: $V_{0.1-0.01} < 0.15$ mL/g, $V_{0.1-0.01}$ corresponding to the cumulative volumes of pores with a size in the range 0.1 μm to 0.01 μm. The pore size corresponds to the diameter of an ideal theoretical pore which is assumed to be cylindrical. Preferably, a porous support is selected which has a pore volume $V_{0.1-0.01} < 0.12$ mL/g; highly preferably, $V_{0.1-0.01} < 0.11$ mL/g.

The fact of having a limited pore volume $V_{0.1-0.01}$, for example $V_{0.1-0.01} < 0.15$ mL/g, and optionally a pore volume $V_{0.01} > 0.2$ mL/g, i.e. a small presence of large mesopores and macropores, means that the entrainment of sulphur deposited in these pores can be limited, the entrainment being due to effluent during use of the capture mass.

The volumes $V_{0.01}$ and $V_{0.1-0.01}$ can be measured by mercury porosimetry [Rouquerol F.; Rouquerol J.; Singh K. Adsorption by powders & porous solids: Principle, methodology and applications, Academic Press, 1999].

The pore volume $V_{0.004}$ may be measured using the following method:

1/ Determining the total pore volume (TPV): a grain density (Dg) is measured using mercury porosimetry, and an absolute density (Dab) is measured using helium pycnometry, then the TPV (mL/g) is calculated as 1/Dg−1/Dab;
2/ Determining the pore volume by mercury porosimetry ($V_{Hg}$) [Rouquerol F.; Rouqerol J.; Singh K. Adsorption by powders & porous solids: Principle, methodology and applications, Academic Press, 1999];

3/ $V_{0.004} = TPV - V_{Hg}$

In accordance with the invention, the porous support has a micropore volume $V_{0.002} < 0.002$ mL/g, preferably $V_{0.002} < 0.001$ mL/g and more preferably $V_{0.002}$ is zero. $V_{0.002}$ corresponds to the cumulative volumes of pores with a size of less than 0.002 μm (i.e. micropores). The pore size corresponds to the diameter of an ideal theoretical pore which is assumed to be cylindrical.

The low $V_{0.002}$ pore volume and the high $V_{0.004}$ pore volume means that the cumulative volume of small mesopores with a diameter in the range 0.002 μm to 0.004 μm can be maximized. Thus, the active sulphur sites present in these small mesopores of the capture mass of the invention are readily accessible to mercury contained in the feed to be treated, meaning that the capture mass can efficiently capture the mercury while avoiding the entrainment of sulphur by the effluent when the capture mass is in use.

The pore volume $V_{0.002}$ may be measured by the t-plot method applied to data obtained from $N_2$ porosimetry [Rouqerol F.; Rouqerol J.; Singh K. Adsorption by powders & porous solids: Principle, methodology and applications, Academic Press, 1999].

Advantageously, the porous support has a total pore volume in the range 0.3 to 1 cm³/g, preferably in the range 0.4 to 0.7 cm³/g.

The specific surface area of the porous support of the capture mass in accordance with the invention, determined by the BET method, is advantageously in the range 100 to 400 m²/g, preferably in the range 150 to 370 m²/g, more preferably in the range 200 to 370 m²/g, still more preferably in the range 250 to 370 m²/g.

The support for the capture mass of the present invention may comprise a quantity of sodium in the range 10 to 5000 ppm by weight of $Na_2O$, preferably a quantity in the range 100 to 5000 ppm, or even in the range 1000 to 5000 pm.

The porous support, and thus the capture mass of the invention, may be in the form of a plurality of elements, each element having the shape of a bead, cylinder, multilobed extrudate, cartwheel, hollow cylinder or any other geometric shape used by the skilled person. Each of the elements constituting the capture mass has the characteristics of the capture mass of the invention. More preferably, the porous support, and thus the capture mass of the invention, is in the form of a plurality of beads with diameters in the range 0.4 to 100 mm, preferably in the range 0.5 to 50 mm, more preferably in the range 0.5 to 10 mm.

The porous support may be shaped using any of the methods known to the skilled person. As an example, the following shaping methods may be used: fluidized bed granulation, high shear rate mixer/granulator, rotary drum, mixing/extrusion, or spheronization.

The capture mass in accordance with the invention may be prepared by depositing the elemental sulphur on the porous support described above, following synthesis pathways which are known to the skilled person. As an example, the following protocols, described in U.S. Pat. No. 4,500,327 and U.S. Pat. No. 4,708,853, may be used, or the protocols described below.

A first protocol for depositing elemental sulphur onto the porous support consists of carrying out the following steps:
  a) mixing solid elemental sulphur powder and porous supports;
  b) heating the mixture in air to a temperature T in the range 110° C. to 220° C. for a period in the range 1 h to 50 h;
  c) bringing the mixture back to ambient temperature.

A second protocol for depositing elemental sulphur onto the porous support consists of carrying out the following steps:
  a) impregnation, by bringing the porous support to between 120° C. and 175° C., preferably 150° C., in contact with sulphur vapour, for example obtained by sublimation of elemental sulphur;
  b) heating the mixture to a temperature T in the range 140° C. to 160° C., preferably to T=150° C., for 90 minutes;
  c) heating the mixture to a temperature T in the range 160° C. to 180° C., preferably to T=170° C., for an additional 45 minutes;
  d) bringing the mixture back to ambient temperature.

The overall description of the preparation of a capture mass in accordance with the invention may, for example, be established as follows:
  a) rapid dehydration of an aluminium trihydroxide (Al(OH)₃) type precursor;
  b) granulation of the alumina obtained from step a);
  c) calcining the porous support obtained from step b) at a T in the range 250° C. to 600° C., preferably in the range 400° C. to 500° C., for example at 450° C.;
  d) impregnation, by bringing the porous support obtained from step c) to a temperature T in the range 120° C. to 175° C., for example to 150° C., in contact with a sulphur vapour obtained by sublimation of elemental sulphur;
  e) heating the mixture obtained from step d) to a temperature T in the range 140° C. to 160° C., for example to a temperature T=150° C. for 90 minutes;
  f) heating the mixture obtained from step e) to a temperature T in the range 160° C. to 180° C., for example to a temperature T=170° C. for an additional 45 minutes;
  g) bringing the mixture back to ambient temperature.

In accordance with the invention, in order to obtain a capture mass with a pore volume $V_{0.004} > 0.1$ mL/g and with a pore volume $V_{0.1-0.01}$ which is preferably less than 0.15 mL/g, the step for depositing sulphur on the porous alumina support is carried out directly after calcining. Preferably, a hydrothermal treatment is not carried out between the step for shaping the support and the calcining step. In fact, in the invention such a hydrothermal treatment would have the unwanted effect of opening the pores and thus of increasing the pore volume $V_{0.1-0.01}$, as taught by patent EP 0 055 164.

The capture mass in accordance with the invention is used to capture heavy metals such as mercury, arsenic or lead contained in a gaseous effluent. The capture mass of the invention is well suited to capturing the mercury contained in a gaseous effluent. The capture mass, for example in the form of a fixed bed disposed in a reactor, is brought into contact with the gaseous effluent to be treated.

Referring to FIG. 1, the gaseous effluent to be treated arriving via the line 1 is introduced into the reactor 2 containing the capture mass of the invention. The bed 2 comprises a plurality of elements each having the characteristics of the capture mass of the invention. The bed of capture mass adsorbs the mercury contained in the effluent so as to obtain a gaseous effluent which is depleted in mercury which is evacuated from the reactor 2 via the line 3. The concentration of mercury in the effluent 3 is lower than the concentration of mercury of the effluent 1.

Figure 2:
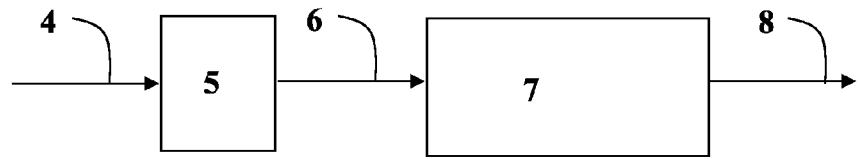
FIG. 2 represents a variation of the process of the invention.

Referring now to FIG. 2, the gaseous effluent to be treated arriving via the line 4 is introduced into a unit 5 in order to reduce the relative humidity of the gaseous effluent. The means 5 may be a water capture mass, for example a molecular sieve based on zeolite. The means 5 may also be a unit that carries out a glycol process. In that case, the gaseous effluent is brought into contact with an absorbent solution comprising glycol, whereupon the solution absorbs water contained in the effluent. As an example, the glycol process described in the document WO 2005/047438 may be used. Alternatively, the means 5 may be a heat exchanger that can be used to raise the temperature of the gaseous effluent, for example by 3° C. to 10° C. The effluent obtained from means 5 is introduced via the line 6 into the reactor 7 containing a bed of capture mass in accordance with the invention. The bed 7 comprises a plurality of elements each having the characteristics of the capture mass of the invention. The bed of capture mass adsorbs the mercury contained in the effluent so as to obtain a gaseous effluent which is depleted in mercury which is evacuated from the reactor 7 via the line 8. The concentration of mercury in the effluent 8 is lower than the concentration of mercury in the effluent 4.

The gaseous effluent treated in accordance with the process of the invention may be combustion fumes, synthesis gas or a natural gas or a hydrocarbon effluent, for example a gaseous oil cut.

The combustion fumes are produced by the combustion of hydrocarbons, biogas, coal in a boiler or by a combustion gas turbine, for example for the purposes of electricity production. These fumes are at a temperature in the range 20° C. to 60° C., a pressure in the range 1 to 5 bars (1 bar=0.1 MPa), and may comprise in the range 50% to 80% of nitrogen, in the range 5% to 40% of carbon dioxide, in the range 1% to 20% of oxygen, and some impurities such as SOx and NOx, if they have not been eliminated downstream by a deacidification process.

The synthesis gas contains carbon monoxide CO, hydrogen $H_2$ (generally in a $H_2/CO$ ratio equal to 2), steam (generally saturated at the temperature at which washing is carried out) and carbon dioxide $CO_2$ (of the order of ten percent). The pressure is generally in the range 20 to 30 bar, but may be as high as 70 bar. It also contains sulphur-containing impurities ($H_2S$, COS, etc), nitrogen-containing impurities ($NH_3$, HCN) and halogenated impurities.

The natural gas is primarily constituted by gaseous hydrocarbons, but may contain several of the following acidic compounds: $CO_2$, $H_2S$, mercaptans, COS, $CS_2$. The quantity of these acidic compounds may vary widely and may be up to 40% for $CO_2$ and $H_2S$. The temperature of the natural gas may be in the range 20° C. to 100° C. The pressure of the natural gas to be treated may be in the range 10 to 120 bar.

The gaseous effluent to be treated in accordance with the invention contains heavy metals, for example mercury, arsenic or lead, in various forms. As an example, mercury is found in the form known as $Hg^0$, corresponding to elemental or atomic mercury, in the molecular form, or in the ionic form, for example $Hg^{2+}$ and its complexes.

The gaseous effluent to be treated contains heavy metals in variable proportions. As an example, the gaseous effluent to be treated, in particular a stream of natural gas, contains between 10 nanograms and 1 gram of mercury per $Nm^3$ of gas.

The gaseous effluent can be brought into contact with the capture mass of the invention at a temperature which is generally in the range −50° C. to 115° C., preferably in the range 0° C. to 110° C. and more preferably in the range 20° C. to 100° C. and at an absolute pressure which is, for example, in the range 0.1 to 200 bars, preferably in the range 1 to 150 bars and highly preferably in the range 10 to 120 bars.

Advantageously, when the gaseous effluent is in contact with the capture mass, the HSV (Hourly Space Velocity, i.e. the volume of gaseous effluent per volume of capture mass per hour) used in the purification process of the invention is in the range 50 to 50000 $h^{-1}$. In the case of a gas feed, the HSV is preferably in the range 50 to 500 $h^{-1}$.

The gaseous effluent to be treated may be moist, i.e. it may contain steam in varying proportions. The hygrometric level in the gaseous effluents is preferably 0 to 100%, preferably 0 to 95% and more preferably 0 to 90%.

The capture mass of the invention is robust with respect to the quantity of water in the feed to be treated, i.e. it is not degraded or degrades only a little and the mercury capture performances remain high even when the gaseous effluent to be treated has a high moisture content. In accordance with the invention, it is possible to treat a moist gaseous effluent with between 60% and 100% relative humidity, or even between 70% and 95%, and up to 80% to 95% relative humidity.

The examples presented below serve to illustrate the function and advantages of the present invention.

EXAMPLE A

Preparation of a Capture Mass $M_1$ in Accordance with the Invention

The capture mass $M_1$ was prepared using a mixture of alumina beads with solid powdered elemental sulphur.
Description of Support:
The support was a flash alumina prepared by granulation, with the characteristics mentioned in Table 1:

TABLE 1

|  | Values |
| --- | --- |
| $Na_2O$ (ppm) | 3450 |
| BET surface area ($m^2/g$) | 321 |
| $V_{0.004}$ (mL/g) | 0.14 |
| $V_{0.002}$ (mL/g) | 0 |
| $V_{0.01}$ (mL/g) | 0.30 |
| $V_{0.1-0.01}$ (mL/g) | 0.10 |
| TPV* (mL/g) | 0.46 |
| WTV** (mL/g) | 0.4 |

*TPV = Total pore volume
The TPV was determined using the following calculation: a grain density (Dg) was measured using mercury porosimetry, and an absolute density (Dab) was measured using helium pycnometry, then the TPV (mL/g) was calculated as 1/Dg − 1/Dab.
**WTV = water take-up volume The WTV was determined by experimentation:
10 g of alumina was placed in a bowl granulator;
a graduated burette was filled with a solution of potassium permanganate, which had been pre-heated to 40° C.;
impregnation was carried out drop by drop over beads rotating in the bowl granulator until a homogeneous deep violet colour appeared (max time=20 min).
Preparation of Capture Mass:
The capture mass $M_1$ was prepared by bringing elemental sulphur into contact with the support. The mixture was heated in air at T=110° C. for 10 h then cooled to ambient temperature.

EXAMPLE B

Preparation of a Capture Mass $M_2$ in Accordance with the Invention

The capture mass $M_2$ was prepared by dry impregnation of alumina beads using a solution containing an emulsion of sulphur.

Description of Support:

The support was a flash alumina prepared by granulation, with the characteristics mentioned in Table 2:

TABLE 2

|  | Values |
|---|---|
| $Na_2O$ (ppm) | 3450 |
| BET surface area ($m^2/g$) | 321 |
| $V_{0.004}$ (mL/g) | 0.14 |
| $V_{0.002}$ (mL/g) | 0 |
| $V_{0.01}$ (mL/g) | 0.30 |
| $V_{0.1-0.01}$ (mL/g) | 0.10 |
| TPV (mL/g) | 0.46 |
| WTV (mL/g) | 0.4 |

Preparation of Solution:

The solution was prepared by mixing 60 g of sulphur into the form of an emulsion in water in order to obtain a solution with a volume equal to 240 mL, corresponding to the water take-up volume of 600 g of support.

Preparation of Capture Mass:

The capture mass $M_2$ was prepared by dry impregnation using 240 mL of the solution described above with 600 g of the alumina beads described above.

The impregnated beads were then dried in a stream of air at 90° C.

EXAMPLE C

Preparation of a Capture Mass $M_3$ (Comparative)

The capture mass $M_3$ was prepared by dry impregnation of alumina beads using a solution containing an emulsion of sulphur.

Description of Support:

The support was a flash alumina prepared by granulation, with the characteristics mentioned in Table 3:

TABLE 3

|  | Values |
|---|---|
| $Na_2O$ (ppm) | 300 |
| BET surface area ($m^2/g$) | 153 |
| $V_{0.004}$ (mL/g) | 0.03 |
| $V_{0.002}$ (mL/g) | 0 |
| $V_{0.01}$ (mL/g) | 0.18 |
| $V_{0.1-0.01}$ (mL/g) | 0.23 |
| TPV (mL/g) | 0.91 |
| WTV (mL/g) | 0.72 |

Preparation of Solution:

The solution was prepared by mixing 45 g of micronized sulphur into the form of an emulsion in water in order to obtain a solution with a volume equal to 432 mL, corresponding to the water take-up volume of 600 g of support.

Preparation of Capture Mass:

The capture mass $M_3$ was prepared by dry impregnation, by bringing 432 mL of the solution described above into contact with 600 g of the alumina beads described above.

The impregnated beads were then dried in a stream of air at 90° C.

EXAMPLE D

Preparation of a Capture Mass $M_4$ (Comparative)

The capture mass $M_4$ was prepared by dry impregnation of alumina beads using a solution containing an emulsion of sulphur.

Description of Support:

The support was a flash alumina prepared by granulation.

TABLE 4

|  | Values |
|---|---|
| $Na_2O$ (ppm) | 320 |
| BET surface area ($m^2/g$) | 198 |
| $V_{0.004}$ (mL/g) | 0.05 |
| $V_{0.002}$ (mL/g) | 0 |
| $V_{0.01}$ (mL/g) | 0.33 |
| $V_{0.1-0.01}$ (mL/g) | 0.31 |
| TPV (mL/g) | 0.70 |
| WTV (mL/g) | 0.55 |

Preparation of Solution:

The solution was prepared by mixing 45 g of sulphur into the form of an emulsion in water in order to obtain a solution with a volume equal to 330 mL, corresponding to the water take-up volume of 600 g of support.

Preparation of Capture Mass:

The capture mass $M_4$ was prepared by dry impregnation, by bringing 330 mL of the solution described above into contact with 600 g of the alumina beads described above.

The impregnated beads were then dried in a stream of air at 90° C.

EXAMPLE E

Preparation of a Capture Mass $M_5$ (Comparative, in Accordance with Document EP 0 107 582)

The capture mass $M_5$ was prepared by dry impregnation of alumina beads using a solution containing an emulsion of sulphur.

Description of Support:

The support was a flash alumina prepared by granulation which had undergone a treatment in an aqueous medium containing nitric acid and acetic acid in the vapour phase at 150° C. for 15 h (see the protocol in patent FR 2 496 631 applied to the preparation of the capture masses claimed in patent EP 0 107 582) before being calcined at 800° C.

TABLE 4

|  | Values |
|---|---|
| $Na_2O$ (ppm) | 565 |
| BET surface area ($m^2/g$) | 132 |
| $V_{0.004}$ (mL/g) | 0.01 |
| $V_{0.002}$ (mL/g) | 0 |
| $V_{0.01}$ (mL/g) | 0.03 |
| $V_{0.1-0.01}$ (mL/g) | 0.71 |
| TPV (mL/g) | 1.01 |
| WTV (mL/g) | 0.95 |

Preparation of Solution:

The solution was prepared by mixing 45 g of sulphur into the form of an emulsion in water in order to obtain a solution with a volume equal to 330 mL, corresponding to the water take-up volume of 600 g of support.

Preparation of Capture Mass:

The capture mass $M_5$ was prepared by dry impregnation, by bringing 330 mL of the solution described above into contact with 600 g of the alumina beads described above.

The impregnated beads were then dried in a stream of air at 90° C.

EXAMPLE F

Residual Loss Tests on the Active Phase of the Capture Masses

For each capture mass, firstly, the proportion of "extractable" active phase was evaluated. To this end, a mass $m_m$ of capture mass being studied, corresponding to a volume ($V_m$=3 cm$^3$) of adsorbents, was disposed in a fixed bed configuration. A stream of gaseous nitrogen was passed through the bed of adsorbents at a flow rate of 300 NL/h, a temperature of 70° C. and a pressure of 20 MPa.

After 3 days, the solid was removed from the fixed bed reactor then weighed ($m_s$). The variations in mass obtained, $\Delta m = m_m - m_s$, for each capture mass were then recorded with respect to the mass of active phase initially present on the capture mass, as follows:

$$\Delta S = (\Delta m \times 100)/(\%S \times m_m/100)$$

Thus, the percentage of active phase, $\Delta S$, which could be extracted from the support during a heavy metals capture operation was obtained. The results are recorded in Table 5.

TABLE 5

| Mass | $\Delta S$/% |
|---|---|
| $M_1$ | 0 |
| $M_2$ | 0 |
| $M_3$ | 3 |
| $M_4$ | 20 |
| $M_5$ | 40 |

This result illustrates the better resistance to loss of active phase of the capture masses of the invention.

EXAMPLE G

Test of Mercury Adsorption Capacity in a Dry Medium on Capture Masses $M_1$, $M_2$, $M_3$ and $M_4$ The mercury adsorption performances of the capture masses prepared as above were tested in a reactor. The capture mass was placed in the fixed bed reactor. A volume $V_m$=3 cm$^3$ of adsorbents was prepared in a fixed bed configuration. A stream of gaseous nitrogen containing a charge, $[Hg]_e$=1060 µg/Nm$^3$ of mercury, was passed through the bed of adsorbents at a flow rate of 300 NL/h, a temperature of 70° C. and a pressure of 20 MPa. The concentration of mercury was measured at the reactor inlet and outlet using a mercury-specific in-line analyser functioning on the atomic fluorescence principle.

These operating conditions were applied to each sample of capture mass until it was saturated. The mercury capture mass was considered to be saturated when the concentrations of mercury at the inlet and at the outlet of the reactor were strictly equal.

It was then possible to evaluate the concentration of mercury $[Hg]_f$ which had become irreversibly chemisorbed onto each capture mass by producing a material balance for the mercury between the reactor inlet and outlet over the whole of the test period. The mercury saturation capacities of the various samples of capture mass are shown in Table 6:

TABLE 6

| Mass | $[Hg]_f$/% by weight with respect to the initial mass of the capture mass |
|---|---|
| M1 | 8.6 |
| M2 | 6.8 |
| M3 | 0 |
| M4 | 1.5 |
| M5 | 0 |

These examples show the higher mercury adsorption capacities which can be obtained using the capture masses of the invention.

EXAMPLE H

Test of Mercury Adsorption in a Moist Medium on the Capture Mass $M_2$

A bead of liquid mercury of approximately 30 g was initially poured into a glass crucible which was then placed in the bottom of a reactor $R_1$. A beaker filled with water was also placed in the bottom of the reactor $R_1$. A mass $m_m$ of the capture mass $M_2$ of the invention was deposited in a cylindrical glass reactor $R_2$ with a volume $V_2$=1 L which was then introduced into the inside of the reactor $R_1$.

The reactor $R_1$ was introduced into a heated chamber regulated to T=70° C. for 1 week.

Figure 3:
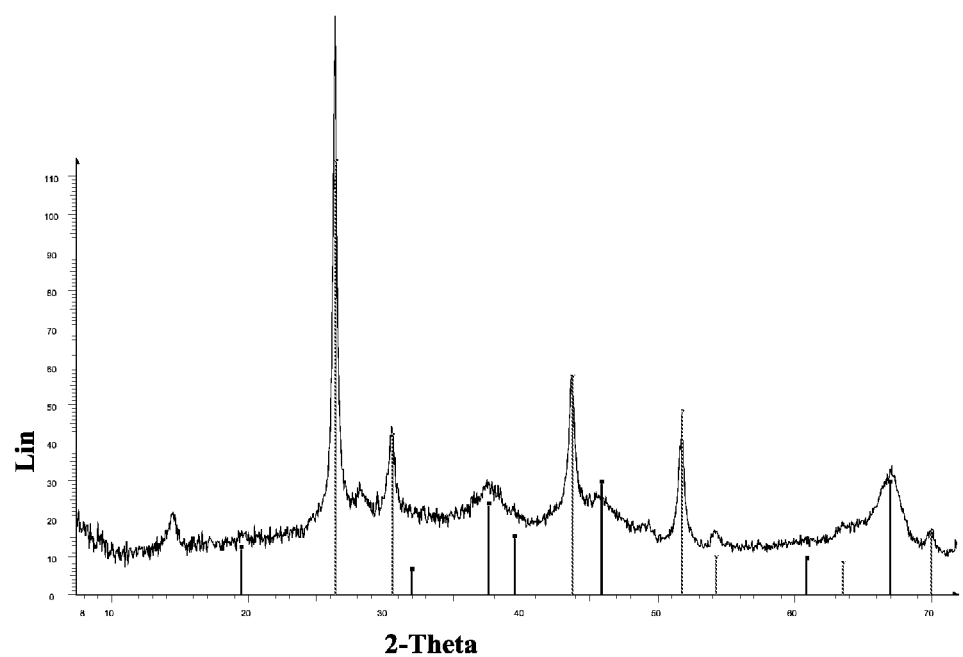
FIG. 3 represents a diffraction spectrum of a capture mass in accordance with the invention which has captured mercury.

The capture mass was then analyzed by X ray diffraction analysis. FIG. 3 represents the measured diffraction spectrum. The angle of the radiation "2-Theta" is shown along the abscissa; the intensity "Lin" of the diffracted radiation is shown up the ordinate. The segments surmounted by a black triangle correspond to the signature of metacinnabar (HgS). Peaks at angles 26.5, 30.5, 43.5 and 51.5 will in particular be observed; they mean that the existence of a crystalline phase of metacinnabar (HgS) obtained from the reaction of elemental mercury with the sulphur deposited on the capture mass can clearly be concluded. In consequence, the capture mass of the invention can be used to capture mercury contained in a moist gaseous phase.

The entire disclosures of all applications, patents and publications, cited herein and of corresponding French application Ser. No. 12/01811, filed Jun. 26, 2012 are incorporated by reference herein.

The invention claimed is:

1. A capture mass for capturing mercury, said mass comprising an active phase deposited on a porous support, the active phase comprising elemental sulphur, the porous support having a pore volume $V_{0.004}$>0.1 mL/g, $V_{0.004}$ corresponding to the cumulative volumes of pores with a size of less than 0.004 µm, and a pore volume $V_{0.002}$<0.002 mL/g, $V_{0.002}$ corresponding to the cumulative volumes of pores with a size of less than 0.002 µm, and a pore volume $V_{0.1-0.01}$<0.15 mL/g, $V_{0.1-0.01}$ corresponding to the cumulative volumes of pores with a size in the range 0.1 µm to 0.01 µm.

2. A capture mass according to claim 1, in which the porous support contains at least one of the following oxides: alumina, titanium oxide, zirconium oxide and silicon oxide.

3. A capture mass according to claim 1, in which the porous support contains alumina.

4. A capture mass according to claim 3, in which the porous support has a total pore volume in the range 0.3 to 1 cm$^3$/g, the porous support has a BET specific surface area in the range 100 to 400 m²/g, and the porous support comprises a quantity of sodium in the range 10 to 5000 ppm by weight of $Na_2O$.

5. A capture mass according to claim 1, in which the porous support has a pore volume $V_{0.002}<0.001$ mL/g, $V_{0.002}$ corresponding to the cumulative volumes of pores with a size of less than 0.002 μm.

6. A capture mass according to claim 1, in which the porous support has a pore volume $V_{0.1}>0.2$ mL/g, $V_{0.1}$ corresponding to the cumulative volumes of pores with a size of less than 0.1 μm.

7. A capture mass according to claim 1, in which the porous support has a pore volume $V_{0.1-0.01}<0.11$ mL/g, $V_{0.1-0.01}$ corresponding to the cumulative volumes of pores with a size in the range 0.1 μm to 0.01 μm.

8. A capture mass according to claim 1, in which the active phase comprises elemental sulphur $S_x$, x being in the range 1 to 30.

9. A capture mass according to claim 1, comprising a quantity by weight of elemental sulphur with respect to the weight of the capture mass which is in the range of 1% to 60%, and the quantity by weight of the porous support with respect to the weight of the capture mass is in the range of 40% to 99%.

10. A process for producing a capture mass according to claim 1, comprising depositing sulphur onto a porous support.

11. A process according to claim 10, in which the sulphur is deposited by bringing a sulphur powder into contact with the support or by bringing a sulphur vapour into contact with the support or by bringing sulphur in liquid solution into contact with the support, then by carrying out a drying step by heating the support containing the sulphur.

12. A process for eliminating mercury contained in a gaseous effluent, comprising bringing into contact a gaseous effluent (1) with the capture mass (2) according to claim 1.

13. A process according to claim 12 in which, before contact, a drying operation (5) is carried out in order to reduce the relative humidity of the gaseous effluent.

14. A process according to claim 13, in which the drying operation is carried out by contact with a water-adsorbing sieve, by contact with an absorbent solution comprising glycol, or by heating the gaseous effluent.

15. A process according to claim 12, in which the contact is carried out at a temperature in the range of −50° C. to 115° C. and at a pressure in the range of 0.1 bar absolute to 200 bars absolute, and with an hourly space velocity in the range of 50 to 50000 $h^{-1}$.

16. A process according to claim 12, in which the relative humidity of the gaseous effluent is in the range of 60% to 100%.

17. A process according to claim 12, in which the gaseous effluent is selected the group consisting of combustion fumes, a synthesis gas, a natural gas and a hydrocarbon effluent.

18. A capture mass according to claim 1, in which the porous support has a pore volume $V_{0.002}$ equal to zero, $V_{0.002}$ corresponding to the cumulative volumes of pores with a size of less than 0.002 μm.

19. A capture mass according to claim 18, in which the porous support has a pore volume $V_{0.1}>0.2$ mL/g, $V_{0.1}$ corresponding to the cumulative volumes of pores with a size of less than 0.1 μm.

20. A capture mass according to claim 18, in which the porous support has a pore volume $V_{0.1-0.01}<0.15$ mL/g, $V_{0.1-0.01}$ corresponding to the cumulative volumes of pores with a size in the range 0.1 μm to 0.01 μm.

* * * * *